United States Patent

Fukuoka et al.

[11] Patent Number: 5,166,393
[45] Date of Patent: Nov. 24, 1992

[54] PROCESS FOR PRODUCING DIARYL CARBONATE

[75] Inventors: Shinsuke Fukuoka; Ryoji Deguchi; Masahiro Tojo, all of Kurashiki, Japan

[73] Assignee: Asahi Kasei Kogyo Kabushiki Kaisha, Osaka, Japan

[21] Appl. No.: 771,538

[22] Filed: Oct. 7, 1991

Related U.S. Application Data

[63] Continuation of Ser. No. 513,422, Apr. 3, 1990, abandoned.

[51] Int. Cl.$^5$ .............................................. C07C 69/96
[52] U.S. Cl. .................................... 558/274; 558/277
[58] Field of Search .............................. 558/274, 277

[56] References Cited

U.S. PATENT DOCUMENTS 4,045,464  8/1977  Romano et al. ................... 558/274
4,552,704  11/1985  Mark ............................. 558/274 X
4,554,110  11/1985  Mark ............................. 558/274 X
4,609,501  9/1986  Mark ............................. 558/274 X

FOREIGN PATENT DOCUMENTS 0338760  10/1989  European Pat. Off. .

Primary Examiner—Jose G. Dees
Assistant Examiner—Joseph M. Conrad, III
Attorney, Agent, or Firm—Birch, Stewart, Kolasch & Birch

[57] ABSTRACT

A process for producing a diaryl carbonate in high yield and with high selectivity which comprises disproportionating an alkylaryl carbonate in the presence of a lead catalyst to produce a diaryl carbonate and a dialkyl carbonate and recovering the diaryl carbonate from the reaction products. Use of the lead catalyst is effective in avoiding corrosion problems normally caused by other catalyst systems.

15 Claims, No Drawings

PROCESS FOR PRODUCING DIARYL CARBONATE

This application is a continuation, of application Ser. No. 07/513,422 filed on Apr. 3, 1990, now abandoned.

BACKGROUND OF THE INVENTION

The present invention relates to a process for producing a diaryl carbonate. More particularly, the present invention relates to a process for producing a diaryl carbonate according to the disproportionation reaction of an alkylaryl carbonate.

It has been already known to obtain diphenyl carbonate by disproportionation of an alkylphenyl carbonate [Japanese Patent Publication No. 48537/1983 (U.S. Pat. No. 4,045,464)]. However, in this method, a catalyst selected from among Lewis acids and transition metal compounds capable of forming Lewis acids is used, and specifically $AlX_3$, $TiX_3$, $UX_4$, $VOX_3$, $VX_5$, $ZnX_2$, $FeX_3$, $SnX_4$ are included, wherein X is a halogen, an acetoxy group, an alkoxy group, or an aryloxy group. Such Lewis acids are highly corrosive to the metallic materials of reaction vessels, pipelines and valves. Thus methods using these Lewis acids involve a problem when industrially practiced.

Further, it has been also proposed to conduct such a method using a catalyst consisting of a mixture of a Lewis acid and a protonic acid [Japanese Laid-open Patent Application No. 173016/1985 (U.S. Pat. No. 4,609,501)]. However, in this method, because a protonic acid is used in addition to a Lewis acid, not only the problem of corrosion becomes more serious, but also separation and recovery of the catalyst are difficult.

Also, some proposals have been made to use organic tin compounds or organic titanium compounds as a catalyst in such methods [Japanese Laid-open Patent Publications Nos. 169444/1985 (U.S. Pat. No. 4,554,110), 169445/1985 (U.S. Pat. No. 4,552,704), 265062/1989, 265063/1989), but these organic tin compounds or organic titanium compounds are difficult to separate completely from the products whereby it is very difficult to obtain the diaryl carbonate with high purity. One important use of a diaryl carbonate is its use as a monomer for producing polycarbonate, and in this case, if an organic tin compound or an organic titanium compound is present, even in a small amount, in the diaryl carbonate, the physical properties of the polycarbonate thus produced will be lowered. Therefore, the diaryl carbonate produced by the methods using such catalysts cannot be effectively used as the monomer for producing the polycarbonate.

Further, it has been also proposed to use in such a method a catalyst selected from a compound containing Sc, Cr, Mo, W, Mn, Au, Ga, In, Bi, Te, and lanthanoid (Japanese Laid-Open Patent Application No. 265064/1989). However the yield of the desired diaryl carbonate is low in this method.

SUMMARY OF THE INVENTION

The above-identified problems have been eliminated by the present invention which provides a process for producing a diaryl carbonate, which comprises disproportionating an alkylaryl carbonate to a diaryl carbonate and a dialkyl carbonate in the presence of a lead catalyst.

DETAILED DESCRIPTION OF THE INVENTION

The process of the present invention is represented by the reaction (I) as shown below:

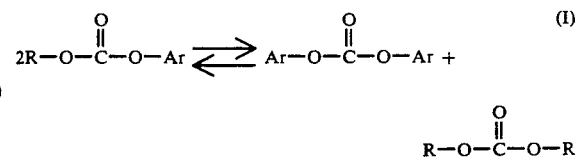

(wherein R represents an alkyl group such as an aliphatic group, an alicyclic group, an aralkyl group, and Ar represents an aryl group which is an aromatic group).

The alkylaryl carbonate to be used as the starting material of the present invention is a compound shown on the left side of the above reaction (I). As R, for example, aliphatic groups including various isomers such as methyl, ethyl, propyl, butyl, pentyl, hexyl, heptyl, octyl, nonyl and the like; alicylic groups such as cyclopropyl, cyclobutyl, cyclopentyl, cyclohexyl, methylcyclobutyl, cyclohexylmethyl and the like; aralkyl groups such as benzyl, phenethyl and the like are preferred. As Ar, unsubstituted aromatic groups such as phenyl, naphthyl, pyridyl, etc.; substituted aromatic groups represented by the following formulae are preferred:

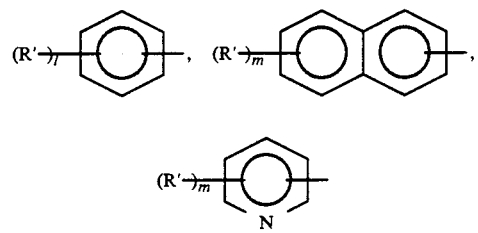

(wherein R' represents a substituent such as lower alkyl group, alkoxy group, acyl group, halogen, aryloxy group, aromatic group, nitro group, cyano group, aralkyl group, etc., l is an integer of 1 to 5, m is an integer of 1 to 7, n is an integer of 1 to 4, and when l, m and n are each an integer of 2 or more, and R' may be either the same or different). Also, in R, those wherein one or more hydrogen is substituted with a substituent such as halogen, alkoxy group having 1 to 10 carbon atoms, cyano group, etc. can be also used.

A particularly preferable alkylaryl carbonate is one where the alkyl group is a lower aliphatic group having 1 to 4 carbon atoms such as methyl, ethyl, propyl, butyl, and where the aryl group is phenyl group or a substituted phenyl group having 7 to 15 carbon atoms with a substituent having 1 to 9 carbon atoms such as methyl, dimethyl, ethyl, t-butyl, 2-phenyl-2-methylethyl, etc.

The lead catalyst to be used in the present invention may be lead containing material or a compound containing lead, but particularly preferable are basic or neutral lead compounds. Examples of such lead compounds preferably used may include lead oxides such as $PbO$, $PbO_2$, $Pb_3O_4$; lead sulfides such as $PbS$, $PbS_2$, $PbS_3$; lead halides such as $PbCl_2$, $PbBr_2$, $PbI_2$, $3PbBr_2.2PbO$, $PbCl_2.Pb(OH)_2$ etc.; lead hydroxides such as $Pb_3O_2(OH)_2$, $Pb_2[PbO_2(OH)_2]$, $Pb_2O(OH)_2$, etc.; plumbites such as $Na_2PbO_2$, $K_2PbO_2$, $NaHPbO_2$, $KHPbO_2$, etc.; plumbates such as $Na_2PbO_3$, $Na_2H_2PbO_4$, $K_2PbO_3$, $K_2[Pb(OH)_6]$, $K_4PbO_4$, $Ca_2PbO_4$, $CaPbO_3$, etc.; carbonates of lead or lead compounds and basic salts thereof such as $PbCO_3$, $2PbCO_3 \cdot Pb(OH)_2$, $PbCO_3 \cdot PbCl_2$, $2PbCO_3 \cdot PbSO_4 \cdot Pb(OH)_2$, etc.; lead salts of organic acids such as $Pb(OCOCH_3)_2$, $Pb(OCOCH_3)_4$, $Pb(OCOCH_3)_2 \cdot PbO \cdot 3H_2O$, etc.; organic lead compounds such as $Bu_4Pb$, $Ph_4Pb$, $Bu_3PbCl$, $Ph_3PbBr$, $Ph_3Pb$ (or $Ph_6Pb_2$), $Bu_3PbOH$, $Ph_2PbO$, etc. (Bu and Ph represent a butyl group and a phenyl group, respectively); lead alkoxides or lead aryloxides such as $Pb(OCH_3)_2$, $Pb(OC_2H_5)_2$, $(CH_3O)Pb(OPh)$, $Pb(OPh)_2$, etc.; alloys of lead such as Pb-Na, Pb-Ca, Pb-Ba, Pb-Sn, Pb-Sb, etc.; lead ores such as galena, boulagerite, etc., and hydrates of these compounds and so on. Of course, these lead compounds may be also those which are reacted with the organic compounds existing in the reaction system such as alkylaryl carbonates, diaryl carbonates, dialkyl carbonates, or hydrolyzed products of these compounds (alcohols, aromatic hydroxy compounds, etc.), and may be also those subjected to heat treatment with the starting material, the products or alcohols or aromatic hydroxy compounds prior to the reaction.

Among these, particularly preferred catalysts are lead and lead compounds such as powdery lead, fine particulate or powdery lead-sodium alloys, various lead oxides, lead hydroxides, lead carbonates and basic lead carbonates, plumbites and plumbates, lead acetates and basic lead acetates, lead alkoxides and lead aryloxides. These lead and lead compounds can be also pretreated by being reacted with organic compounds which exist in the reaction system, or by being subjected to a heat treatment with the starting material, with the products or with alcohols or aromatic hydroxy compounds and used as the catalyst system. In the present invention, when these particularly preferred catalysts are used, not only can a diaryl carbonate be obtained in high yield and high selectivity, but also the diaryl carbonate can be easily separated from the catalysts used. More specifically, the diaryl carbonate thus produced is generally separated and purified by distillation under reduced pressure from the reaction mixture, and none of the lead components of these particularly preferred catalysts is distilled off together with the diaryl carbonate, because there is entirely no or very little vapor pressure of the lead components under such distillation conditions. Accordingly, a highly pure diaryl carbonate free from any lead components can be obtained. This is one of the excellent features of the present invention.

The catalyst of the present invention is excellent in producing a diaryl carbonate in a high yield with high selectivity, and further it has also the specific feature that there is no problem of corrosion of the metallic materials of the installation caused by the prior art use of a Lewis acid, because the lead and lead compounds constituting the catalyst are neither Lewis acids nor transition metal compounds which can form Lewis acids.

The catalyst comprising such lead materials or lead compounds can be used either singly or as a mixture of two or more kinds.

The amount of the lead catalyst to be used in the present invention is not particularly limited, but may be generally used in the range of from 0.00001 to 100 moles, preferably from 0.001 to 2 moles per mole of the alkylaryl carbonate used.

Since the reaction of the present invention is an equilibrium reaction as shown by the reaction (I), by removing at least one of the diaryl carbonate or the dialkyl carbonate which are the reaction products from the reaction system, the reaction can better progress.

Since the reaction of the present invention is generally carried out in liquid phase or gas phase, it is preferable to progress the reaction while distilling off the component with the lower boiling point of the reaction products. The order of the boiling points of the starting materials and the products are generally diaryl carbonate > alkylaryl carbonate > dialkyl carbonate, or dialkyl carbonate > alkylaryl carbonate > diaryl carbonate, and thus it is easy to distill off one of the products. A dialkyl carbonate of which the alkyl group comprises a lower aliphatic group such as methyl, ethyl, propyl, butyl, etc. has a low boiling point, and therefore can be easily distilled off from the reaction system. In such meaning, an alkylaryl carbonate having a lower aliphatic group may be preferably used.

For effectively distilling off the lower boiling components, there may be preferably employed the method in which an inert gas such as nitrogen, helium, carbon dioxide, etc. or a lower hydrocarbon gas or mixture thereof is introduced into the reaction system, and the method is performed under reduced pressure. These methods may be also used in combination. In the case of a tank type reactor, it is also a preferable method to perform effective stirring to increase the interfacial area between the gas and liquid phases, or to promote the interfacial renewal, while in the case of a tower type reactor, it is also a preferable method to make an apparatus with a large interfacial area between the gas and liquid phases.

The reaction of the present invention is generally carried out at about 50° to about 400° C., preferably in the range of from about 80° to about 300° C. The reaction time which may vary depending on the reaction system employed and other reaction conditions chosen is typically about one minute to about 50 hours. The reaction pressure may be either reduced pressure, normal pressure or in the range of from about 0.01 kg/cm$^2$ to about 50 kg/cm$^2$.

The process of the present invention can also be practiced with or without the use of solvent. When a solvent is used, it is also a preferable method to distill off the lower boiling products together with a part of the solvent. Examples of such solvent may include aliphatic hydrocarbons such as pentane, hexane, heptane, octane, nonane, decane, undecane, tridecane, etc.; aromatic hydrocarbons such as benzene, toluene, xylene, ethylbenzene, styrene, etc.; alicyclic hydrocarbons such as cyclohexane, methylcyclohexane, etc.; halogenated hydrocarbons such as methyl chloride, methylene chloride, chloroform, carbon tetrachloride, dichloroethane, chlorobenzene, dichlorobenzene, etc.; nitrilies such as acetonitrile, propionitrile, benzonitrile, etc.; ketones such as acetone, methyl ethyl ketone, acetophenone, etc.; ethers such as diethyl ether, tetrahydrofuran, dioxane, diphenyl ether. etc.

The process of the present invention can be practiced by either a batch system or a continuous system.

DETAILED DESCRIPTION OF THE PREFERRED EMBODIMENTS

The present invention is described in more detail by referring to the following examples, which should not be considered as limiting in any way the sense of the present invention.

EXAMPLE 1

Pre-treatment of the catalyst is performed by heating 2 g of PbO and 10 g of methylphenyl carbonate under a small amount of nitrogen stream at about 180° C. for one hour. Subsequently, by distilling off unreacted methylphenyl carbonate and most of the diphenyl carbonate formed at about 150° C. under a reduced pressure of about 0.5 mm Hg, 2.5 g of a pale yellow solid is obtained. To this is added 76 g (0.5 mole) of methylphenyl carbonate, and the whole amount is transferred into a 200 ml four-necked flask equipped with a stirring device, a reflux condenser, a gas introducing inlet reaching lower level than the liquid surface, and a thermometer. The reaction is carried out by dipping the flask in an oil bath of 190°–195° C. under stirring, while introducing dry nitrogen at a rate of 80N ml/min. Through the jacket of the reflux condenser is conveyed water at a temperature of about 90° C., and the reaction is carried out while distilling off dimethyl carbonate by-produced, and refluxing methylphenyl carbonate and the diphenyl carbonate formed to return them into the reactor. The results are shown in Table 1. Selectivity of anisole which is the by-product is 1% or less even after 3 hours.

TABLE 1

| Reaction time (min.) | Methylphenyl carbonate conversion (%) | Diphenyl carbonate Yield (%) | Selectivity (%) |
| --- | --- | --- | --- |
| 30 | 56.6 | 56.2 | 99.3 |
| 60 | 74.5 | 73.9 | 99.2 |
| 120 | 85.5 | 84.7 | 99.1 |
| 180 | 90.8 | 89.9 | 99.0 |

Three hours later, the system is gradually brought under reduced pressure to distill off unreacted methylphenyl carbonate. Subsequently, in place of the reflux condenser, a packed column with an inner diameter of 2 cm and a height of 30 cm (packed with 6 mm$\phi$ Dickson packings made of stainless steel) is mounted, and distillation is performed under reduced pressure to give 45 g of diphenyl carbonate (purity 99.99%) which is distilled out at 184°–185° C./17 mm Hg. When metal analysis in the diphenyl carbonate is conducted by ICP (Inductively coupled discharge spectrometry) method, no lead is detected at all.

COMPARATIVE EXAMPLE 1

The disproportionation reaction of methylphenyl carbonate (76 g, 0.5 mole) is carried out in the same manner as in Example 1, by using of 3.8 g of Ti-(OC$_6$H$_5$)$_4$ as the catalyst proposed in U.S. Pat. No. 4,045,464. As a result, the conversion of methylphenyl carbonate after 3 hours is found to be 60.3%, and the yield of diphenyl carbonate 56.1% and its selectivity 93.0%. Anisole which is the by-product is found to be formed at a selectivity of 6.2%. Subsequently, similarly as in Example 1, unreacted methylphenyl carbonate is distilled off, and 23 g of diphenyl carbonate (purity 99.0%) is obtained by reduced pressure distillation. When metal analysis in the diphenyl carbonate is conducted by the ICP method, 150 ppm of Ti is detected.

EXAMPLE 2–11

According to the same procedure as in Example 1 except for using various lead compounds or lead in place of PbO, the reactions from methylphenyl carbonate (76 g) to diphenyl carbonate are carried out. The results of the reactions after 2 hours are listed in Table 2. In these Examples, the catalyst is used in an amount of 5 mmol or 5 mg-atom as lead. The Pb-Na alloy used in Example 3 contained 90% by weight of Pb. In Examples 2, 3, 7, 8 and 9, the reaction is carried out directly without pre-treatment of the catalyst.

TABLE 2

| Example | Catalyst | Methylphenyl carbonate conversion (%) | Diphenyl carbonate Yield (%) | Selectivity (%) |
| --- | --- | --- | --- | --- |
| 2 | Powdery Pb | 52.3 | 51.8 | 99.0 |
| 3 | Fine particulate Pb—Na alloy | 88.2 | 81.1 | 92.0 |
| 4 | PbO$_2$ | 86.5 | 85.7 | 99.1 |
| 5 | Pb$_3$O$_4$ | 82.3 | 81.4 | 98.9 |
| 6 | Pb(OH)$_2$ | 87.8 | 87.1 | 99.2 |
| 7 | 2PbCO$_3$.Pb(OH)$_2$ | 85.6 | 83.3 | 97.3 |
| 8 | Pb(OAc)$_2$.Pb(OH)$_2$ | 84.5 | 82.0 | 97.0 |
| 9 | Pb(OAc)$_2$.3H$_2$O | 85.0 | 82.0 | 96.5 |
| 10 | Na$_2$PbO$_3$ | 80.2 | 79.4 | 99.0 |
| 11 | PbCO$_3$ | 83.0 | 82.0 | 98.8 |

EXAMPLES 12–17

The reactions are carried out in the same manner as in Example 1 except for using various alkylaryl carbonates in place of methylphenyl carbonate, and the results of the reactions after 2 hours are shown in Table 3.

TABLE 3

$$R-OCO-Ar$$

| Example | R | Ar | Diaryl carbonate Yield (%) | Selectivity (%) |
| --- | --- | --- | --- | --- |
| 12 | C$_2$H$_5$ | —C$_6$H$_5$ | 76.5 | 98.5 |
| 13 | n-C$_3$H$_7$ | —C$_6$H$_4$—CH$_3$ | 70.2 | 97.0 |
| 14 | CH$_3$ | —C$_6$H$_4$—C(CH$_3$)$_3$ | 86.0 | 99.0 |
| 15 | CH$_3$ | —C$_6$H$_4$—C(CH$_3$)$_2$—C$_6$H$_5$ | 88.5 | 98.8 |
| 16 | CH$_3$ | —C$_6$H$_4$—Cl | 84.0 | 97.0 |
| 17 | CH$_3$ | —C$_6$H$_4$—OCH$_3$ | 85.8 | 97.5 |

However, in Examples 12 and 13, the reaction temperature is 205°–210° C., and an oil of about 130° C. is circulated through the reflux condenser.

EXAMPLE 18

Into a flask equipped with a stirrer and a gas outlet is charged 578 g of phenol, and the flask is dipped in an oil bath. The oil bath is heated to about 110° C., and 100 g of PbO is added little by little under stirring. The oil bath is heated to reach 190° C. in 3 hours. Water and phenol are distilled off. When the amount of distilled liquid becomes 406 g, distillation is stopped, and after cooled to about 110° C., 300 ml of toluene is added and the mixture is cooled to room temperature. As a result, pale yellow crystals are precipitated. By recrystallization of the crystals by use of 350 ml of toluene, 120 g of crystals are obtained. The Pb content in the crystals is found to be 52.7% by ICP analysis. The crystals are identified to be $Pb(OC_6H_5)_2$.

The reaction is carried out in the same manner in Example 1 except for using 2 g of $Pb(OC_6H_5)_2$, 100 g of n-butylphenyl carbonate, making the reaction temperature 205°–210° C., the reaction pressure 80 mm Hg, and passing oil at a temperature of about 140° C. through the jacket of the reflux condenser. One hour later, the conversion of n-butylphenyl carbonate is found to be 80.8%, and the yield of diphenyl carbonate is 80.0%, with its selectivity being 99.1%.

According to the present invention, by use of a lead catalyst, a diaryl carbonate can be produced in a high yield with high selectivity, and the problems of corrosion, etc. of the apparatus caused by the use of a catalyst such as Lewis acid has been solved. Furthermore, according to the present invention, a highly pure diaryl carbonate required for the production of polycarbonate with high qualities can be easily obtained.

What we claim is:

1. A process for producing a diaryl carbonate which comprises disproportionating an alkylaryl carbonate at a temperature of about 50° to about 400° C. under a reduced pressure of 0.01 kg/cm$^2$ to about 50 kg/cm$^2$ in the presence of a lead catalyst comprising lead or at least one lead compound selected from the group consisting of lead sulfides, lead halides, lead hydroxides, plumbites, plumbates, lead carbonates, lead salts of organic acids, organic lead compounds with alkyl-lead bonds or aryl-lead bonds, wherein said alkyl-and aryl- respectively represent an alkyl group having 3 to 10 carbon atoms and an aryl group having 6 to 12 carbon atoms alloys of lead, and lead ores to produce a diaryl carbonate and a dialkyl carbonate, and recovering the diaryl carbonate from the reaction products.

2. The process of claim 1, wherein the disproportionating of the alkylaryl carbonate is conducted at a temperature of about 80° to 300° C.

3. The process according to claim 1, wherein lead and a neutral or basic lead compound are used as the lead catalyst.

4. The process according to claim 1, wherein the alkyl group in said alkylaryl carbonate and in said dialkyl carbonate is an aliphatic group having 1 to 4 carbon atoms.

5. The process according to claim 1, wherein the aryl group in said alkylaryl carbonate and in said diaryl carbonate is a phenyl group or a substituted phenyl group having 7 to 15 carbon atoms.

6. A process for producing a diaryl carbonate which comprises disproportionating an alkylaryl carbonate at a temperature of about 50° to 400° C. under a reduced pressure of 0.01 kg/cm$^2$ to about 50 kg/cm$^2$ in the presence of a lead catalyst comprising at least one lead compound selected from lead oxides to produce a diaryl carbonate and a dialkyl carbonate, and recovering the diaryl carbonate from the reaction products.

7. The process according to claim 6, wherein lead oxide subjected to a heat treatment with at least one organic compound selected from the group consisting of alkylaryl carbonates, diaryl carbonates, dialkyl carbonates, aliphatic hydroxy compounds and aromatic hydroxyl compounds, is used as the catalyst.

8. The process of claim 6, wherein the disproportionating of the alkylaryl carbonate is conducted at a temperature of about 80° to 300° C.

9. The process according to claim 6, wherein the alkyl group in said alkylaryl carbonate and in said dialkyl carbonate is an aliphatic group having 1 to 4 carbon atoms.

10. The process according to claim 6, wherein the aryl group in said alkylaryl carbonate and in said diaryl carbonate is a phenyl group or a substituted phenyl group having 7 to 15 carbon atoms.

11. A process for producing a diaryl carbonate which comprises disproportionating an alkylaryl carbonate at a temperature of about 50° to 400° C. under a reduced pressure of 0.01 kg/cm$^2$ to about 50 kg/cm$^2$ in the presence of a lead catalyst comprising at least one lead compound selected from the group consisting of lead alkoxides or lead aryloxides to produce a diaryl carbonate and a dialkyl carbonate, and recovering the diaryl carbonate from the reaction products.

12. The process according to claim 11, wherein the lead aryloxide is lead diphenoxide.

13. The process of claim 11, wherein the disproportionating of the alkylaryl carbonate is conducted at a temperature of about 80° to 300° C.

14. The process according to claim 11, wherein the alkyl group in said alkylaryl carbonate and in said dialkyl carbonate is an aliphatic group having 1 to 4 carbon atoms.

15. The process according to claim 11, wherein the aryl group in said alkylaryl carbonate and in said diaryl carbonate is a phenyl group or a substituted phenyl group having 7 to 15 carbon atoms.

* * * * *